(12) United States Patent
Tesch

(10) Patent No.: US 7,475,595 B1
(45) Date of Patent: Jan. 13, 2009

(54) UNDERWATER WEIGHING APPARATUS

(76) Inventor: Jeffery C. Tesch, 31144 Old Mill Rd., Dresbach, MN (US) 55947

(*) Notice: Subject to any disclaimer, the term of this patent is extended or adjusted under 35 U.S.C. 154(b) by 0 days.

(21) Appl. No.: 11/897,885

(22) Filed: Sep. 4, 2007

(51) Int. Cl.
G01N 9/10 (2006.01)
G01N 9/20 (2006.01)
A61B 5/00 (2006.01)
A61B 5/103 (2006.01)
G01G 5/02 (2006.01)
G01G 5/04 (2006.01)

(52) U.S. Cl. ............... 73/437; 177/207; 600/300; 600/587

(58) Field of Classification Search ............ 177/207; 600/300, 587; 73/437
See application file for complete search history.

(56) References Cited

U.S. PATENT DOCUMENTS

| | | | | |
|---|---|---|---|---|
| 607,010 | A * | 7/1898 | Baumann | 177/207 |
| 2,936,164 | A * | 5/1960 | Di Giorgio | 177/207 |
| 3,068,683 | A * | 12/1962 | Petterson, Jr. et al. | 73/1.28 |
| 4,233,743 | A * | 11/1980 | Flick | 33/512 |
| 4,372,405 | A * | 2/1983 | Stuart | 177/25.14 |
| 4,753,307 | A * | 6/1988 | Muehlenbein | 177/244 |
| 4,770,041 | A * | 9/1988 | Bearce | 73/437 |
| 4,873,866 | A * | 10/1989 | Fairbanks | 73/437 |
| 6,516,221 | B1 * | 2/2003 | Hirouchi et al. | 600/547 |
| 7,296,466 | B2 * | 11/2007 | Kusumoto | 73/437 |
| 2002/0151803 | A1 * | 10/2002 | Kouou | 600/483 |
| 2008/0234552 | A1 * | 9/2008 | Averbach | 600/300 |

FOREIGN PATENT DOCUMENTS

JP 2003-265427 A * 9/2003

* cited by examiner

Primary Examiner—Randy W Gibson
(74) Attorney, Agent, or Firm—William J. Ryan

(57) ABSTRACT

A portable underwater weighing apparatus is provided comprising a buoyant frame having sufficient buoyancy to support the apparatus and the weight of a person being weighed upon the surface of water, said frame defining a central opening therein; a support member attached to said frame and extending across said central opening; a weighing platform suspended from said support member within said central opening by means of suspension members; and load cells located along each of said suspension cables for measuring the relative load upon said cables when a person to be weighed is positioned on said weighing platform.

8 Claims, 3 Drawing Sheets

UNDERWATER WEIGHING APPARATUS

BACKGROUND OF THE INVENTION

The present invention relates to an underwater weighing apparatus useful in determining the body density of the person being weighed.

It is medically useful to estimate the body fat content of a person as the relative amount of their body fat changes due to diet, exercise, disease or aging. It is well known in the art to weigh persons under water as a means of determining the body fat content of the person being weighed. Body fat is less dense than water whereas the fat free portion of the body (including muscle, bone, etc.) is more dense than water. By weighing a person who is totally immersed in water, conclusions can be drawn as to the relative amounts of body fat of the person. It has been generally accepted that the most accurate way to assess the relative fat content of a person is to measure the overall body volume by means of water displacement, correct for the volume of gas in the body, and calculate the body density by dividing the mass of the body by its (corrected) volume.

Conventional methods of weighing persons under water generally require a pool or specially constructed immersion tank, sufficiently large to accommodate a person seated or kneeling on a weighing chair or platform, and containing a sufficient amount of water to totally immerse the person being weighed. Such conventional methods involving pools generally require a weighing apparatus to be suspended from the ceiling, or from an overhead boom, or otherwise attached to the pool. The means of attaching such weighing apparatuses are cumbersome and required rigid, fixed attachment to the ceiling of the room in which the pool is located or the sides or bottom of the pool. Since a variety of sizes and shapes of pools or tanks have been constructed for the purpose of weighing persons under water, each pool or tank required a uniquely designed weighing system which was more or less permanently fixed in place and not easily moved. As a result, conventional immersion tanks and underwater weighing systems are expensive and usually found only at universities where research on the relative amount of body fat is conducted.

It is desirable to have a simple, light-weight and portable apparatus which can be used in conventional pools or tanks of water.

BRIEF SUMMARY OF THE INVENTION

It is one object of the present invention to provide an underwater weighing apparatus which is not fixed to the structure of the pool or tank or the room in which it is located.

It is another object of the present invention to provide an underwater weighing apparatus which is easily portable and may be utilized in a variety of locations where a suitable pool or tank of water is available.

It is a further object of the present invention to provide an underwater weighing apparatus that is lower in cost than conventional weighing systems, thereby permitting the use of such apparatus in high schools, health clubs or other locations having an existing swimming pool or therapy tank.

It is a further object of the present invention to provide an underwater weighing apparatus which is constructed of lightweight materials to facilitate placement into and removal from a pool or tank.

To those ends, a portable underwater weighing apparatus is provided which comprises a buoyant frame adapted to float upon the surface of the water while supporting a weighing platform upon which a person being weighed is placed. A support bracket is attached to and extends upwardly from the buoyant frame. The support bracket comprises a pair of oppositely disposed vertical members, each of which is attached to an opposite side of the frame, and a horizontal cross member connecting the tops of the vertical members. In this manner, the cross member is located above and parallel to the surface of the water when the frame is in place for use. A weighing platform, having a seat portion upon which the person being weighed may be seated and side brackets extending upwardly from opposed sides of the seat portion, is suspended from the cross member by suspension means comprising one or more suspension cables having an electronic load cell, the suspension means being attached at one end to the cross member and at the other end to the side brackets of the weighing platform. The load cells are of type wherein the load on the load cell is measured by change in electrical transmission characteristics of the cell when under load. The change in the electrical transmission characteristics of the load cell when a person is being weighed is transmitted from the load cells to a computer by means of electrical communications (i.e., wires or wireless) to measure the relative load on the load cells. The computer contains a program to calculate the weight of the person being weighed from the signal received from the load cells.

DETAILED DESCRIPTION OF THE PREFERRED EMBODIMENT

Figure 1:
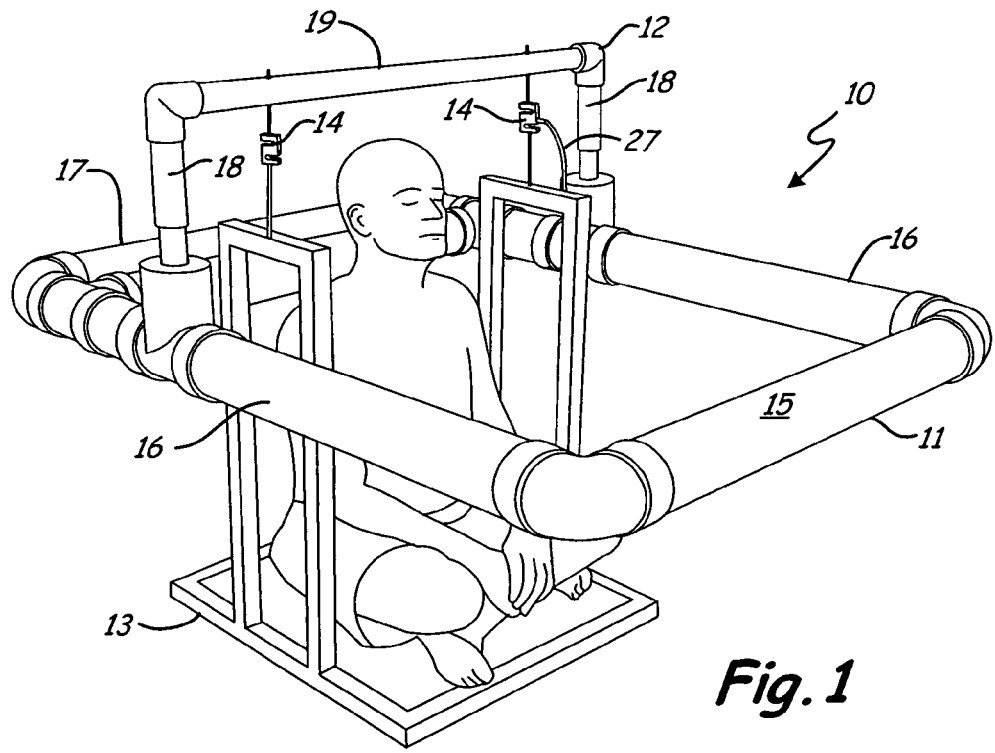
FIG. 1 is an elevational view of an underwater weighing apparatus according to the present invention showing a person being weighed.
Figure 2:
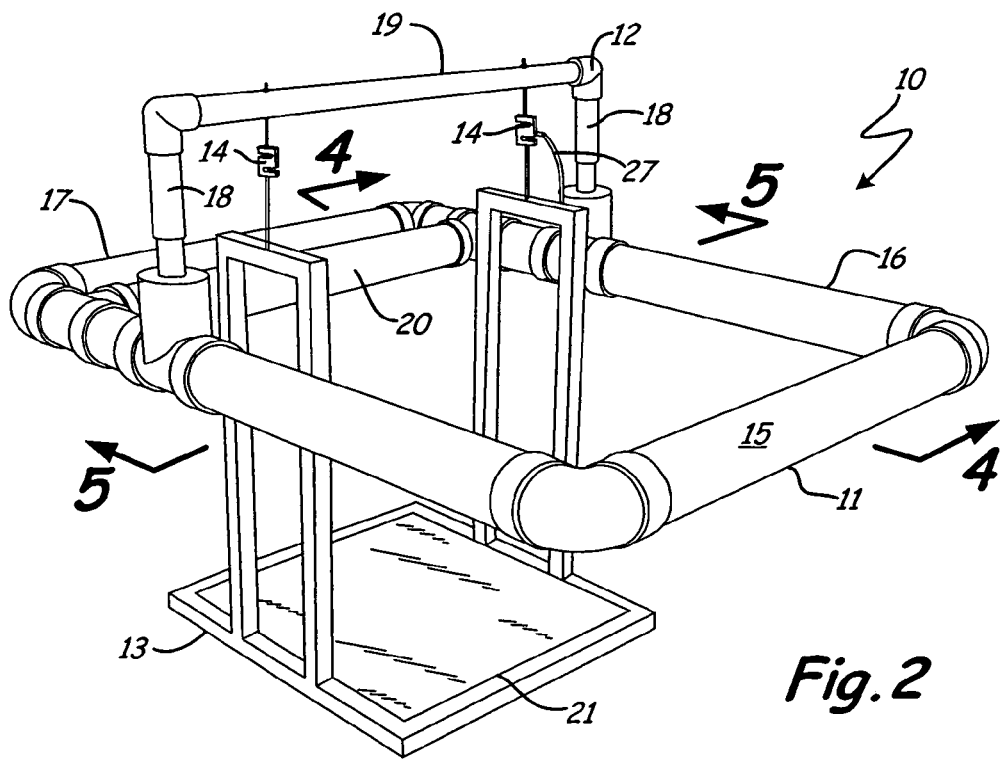
FIG. 2 is an elevational view of an underwater weighing apparatus according to the present invention.
Figure 3:
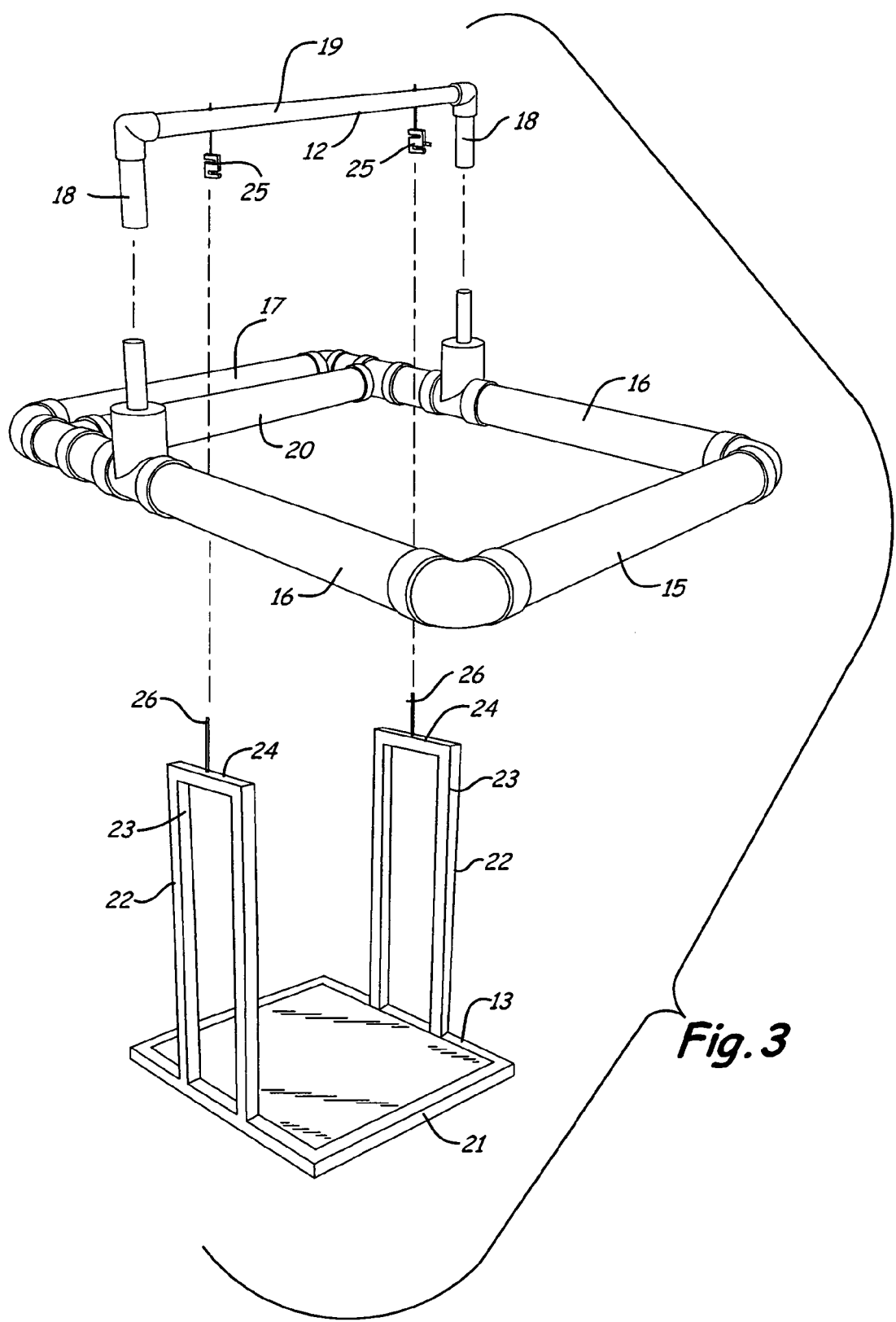
FIG. 3 is an exploded view showing an underwater weighing apparatus according to the present invention showing frame, cross bar with two load cells attached and weighing platform.
Figure 4:
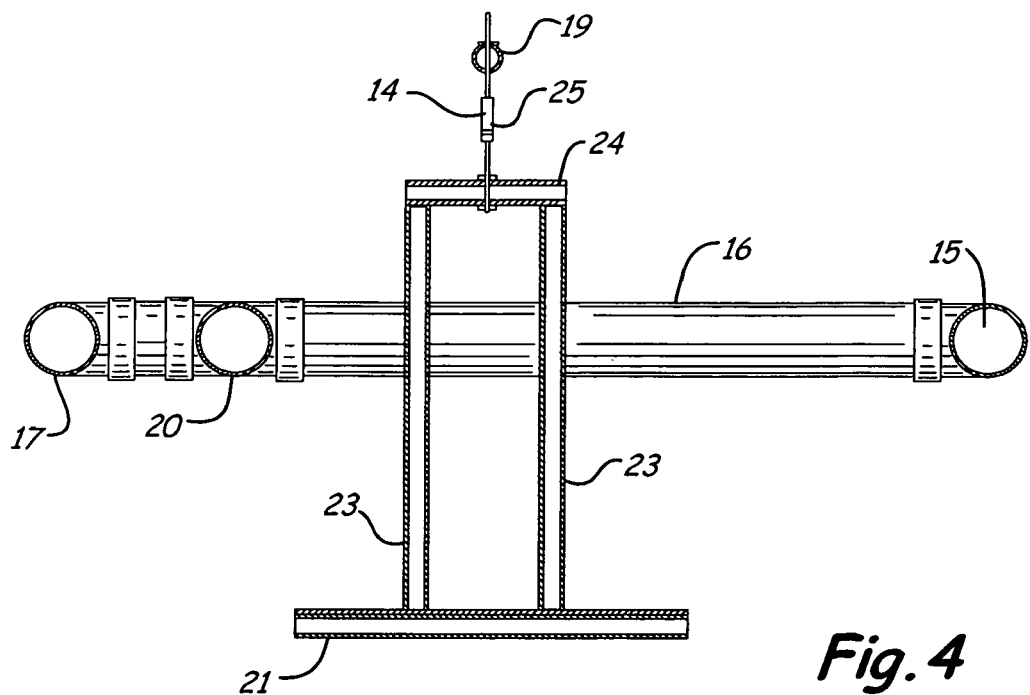
FIG. 4 is a cross sectional view of an underwater weighing apparatus according to the present invention taken along the line 4-4 in FIG. 2.
Figure 5:
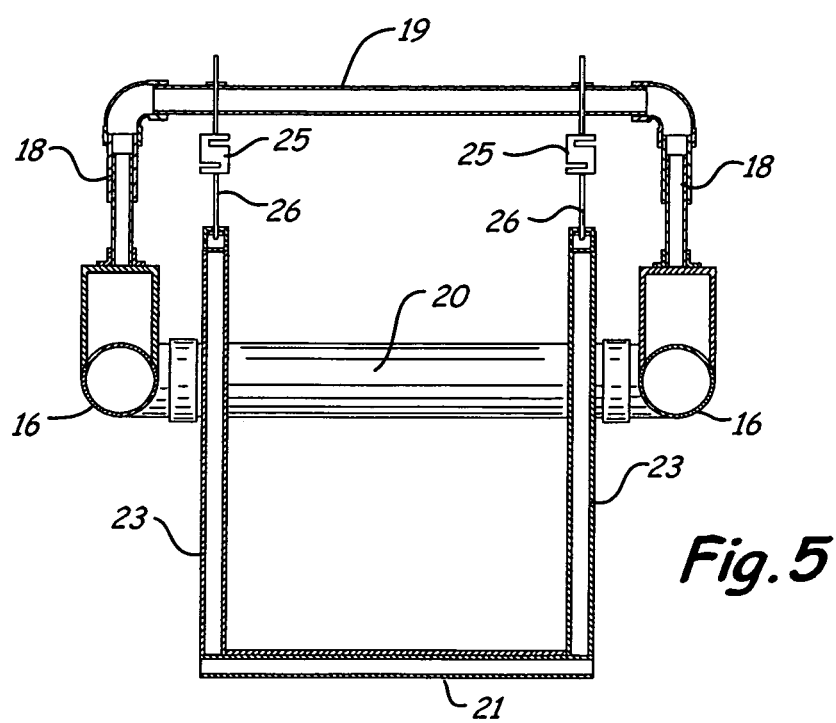
FIG. 5 is a cross sectional view of an underwater weighing apparatus according to the present invention taken along the line 5-5 in FIG. 2.

Referring to the drawing, wherein like numerals represent like elements throughout the several views, there is shown an underwater weighing apparatus generally designated by the numeral 10. Apparatus 10 comprises a buoyant frame 11 defining a central opening, a support bracket 12 attached across the top of frame 11, a weighing platform 13 suspended from support bracket 12 and weight measuring means 14 connected between support bracket 12 and weighing platform 13. Frame 11 has sufficient buoyancy to float upon the surface of water while supporting the weight of the apparatus 10 and a person being weighed. Frame 11 may advantageously be constructed of hollow tubing, similar to that used in plumbing applications (i.e., PVC tubing), having sufficient dimensions to provide the necessary buoyancy. It will be understood, however, that any suitable material providing the necessary buoyancy may be used within the scope of my invention.

Frame 11 is sized to receive weighing platform 13 and the person being weighed within the central opening, as best seen in FIG. 1. Frame 11 may be advantageously rectangular in shape, having a front portion 15, parallel side portions 16 and rear portion 17. It will be further understood that frame 11, however, may have different configurations within the scope on my invention.

Support bracket 12 comprises a pair of spaced, vertical members 18 attached at their lower ends to opposite side portions 16 of frame 11 and extending upwardly therefrom, and a cross member 19 attached across the top ends of vertical members 18. Support bracket 12 is attached to frame 11 in such a manner that cross member 19 extends across the center of the central opening in frame 11 for optimal positioning of the person being weighed for stability purposes when apparatus 10 is supported upon the surface of water.

Support bracket 12 is preferably offset rearwardly from the center of frame 11 to provide sufficient space within the central opening defined by frame 11 for access to the weighing platform 13 by the person being weighed and to permit the person being weighed to bend forward while being weighed, as discussed below. An additional rear buoyant member 20 is located adjacent to rear portion 17 of frame 11 to provide additional buoyancy to counteract the effect of the rearward shift of the center of gravity of apparatus 10 resulting from the rearward offset of support bracket 12.

Weighing platform 13 comprises a seat portion 21 and a pair of side brackets 22 attached to opposite sides of seat portion 21 and extending at right angles to the plane of seat portion 21. Each of the side brackets 22 has spaced, parallel upright members 23 attached at their lower ends to a side of seat portion 21 and a horizontal member 24 attached across the upper ends of the corresponding upright members 23. The spacing of upright members 23 in this manner imparts stability to seat portion 21 when apparatus 10 is in use. Weighing platform 13 may be advantageously constructed of tubular PVC members and a perforated sheet of plastic or other suitable material.

Weight measuring means 14 comprises a pair of spaced load cells 25 attached to cross member 19 near its outer ends and suspension cables 26 attached at one end to one of the load cells 25 and at the other end to the center of the horizontal member 24 of one of the side brackets 22. The connection of load cells 25 to cross member 19 and suspension cables 26 to horizontal members 24 may be accomplished by means of threaded studs eyebolts and hooks, or any other suitable means. Although I have disclosed two load cells in the embodiment described herein, it will be apparent to those skilled in the art that more or less load cells may be used within the scope of my invention.

Load cells 25 are of the type that wherein the electrical conductivity characteristics across the load cell 25 vary according to the load (or weight) applied across the load cell 25. By measuring the change in electrical conductivity characteristics, the change in load carried by the load cell 25 can be calculated. This is accomplished by applying an electrical current across the load cell 25 when unloaded and when loaded, measuring the difference between the electrical conductivity characteristics and determining the size of the load based on those differences. Electrical signaling means 27 are attached to each load cell 25 to report the altered electrical conductivity characteristics to a computer (not shown) which is capable of calculating the change in weight between the unloaded and loaded states of the apparatus 10.

In use, frame 11 is placed upon a body of water having sufficient size to accommodate and float the assembled apparatus 10 and the person being weighed. Weighing platform 13 is suspended from cross member 19 as indicated above. Weight measuring means 14 are calibrated to "zero" to allow for the inherent weight of weighing platform 13 itself. Since it is possible that the person to be weighed will have a positive buoyancy, depending upon his/her body makeup, it is necessary that the weight of the weighing platform 13 in water be sufficient to maintain a positive load on the load cells 25 when a buoyant person is placed on weighing platform 13. If the weighing platform 13 is too light, no load is applied to the load cells 25 when a person with a sufficiently positive buoyancy is placed on the weighing platform 13. As a result, the weighing platform 13 is typically weighted with sufficient ballast to insure that there is always a positive load on load cells 25, even when buoyant persons are weighed. Once the apparatus 10 is calibrated to "zero," the person to be weighed enters the water and is positioned upon weighing platform 13. Immersed persons can be weighed under water with any volume of air in their lungs as long as the volume is accounted for. Typically, the person being weighed exhales to eliminate as much air as possible from his/her lungs and totally submerges his/her head and upper body under water. Once so positioned, electrical currents are applied across the load cells 25 and the changes in electrical conductivity characteristics are measured to determine the relative submerged weight of the person. Information concerning the changes in electrical conductivity of load cells 25 is transmitted by conventional means (either wires or wireless) to a computer (not shown) which contains a program to interpret that information and draw conclusions as to the relative body fat of the person weighed.

While I have described the preferred embodiment of my invention, it will be evident to those skilled in the art that other embodiments may be possible within the scope of my invention.

What is claimed is:

1. An underwater weighing apparatus for measuring the relative amount of body fat of a person being weighed, comprising:
    (a) a buoyant member having sufficient buoyancy to support the apparatus and the weight of the person being weighed upon the surface of water;
    (b) a weighing platform for receiving the person to be weighed;
    (c) support means for suspending said weighing platform from said buoyant member; and
    (d) weighing means for measuring the weight of a person positioned upon said weighing platform.

2. An underwater weighing apparatus according to claim 1, wherein an opening is defined within said buoyant member and said support means comprises a support member attached to said buoyant member and extending across said opening, wherein said weighing platform is suspended from said support member within said opening by one or more cables.

3. An underwater weighing apparatus according to claim 1, wherein said weighing means comprises a load cell located upon each of said cables.

4. An underwater weighing apparatus for measuring the relative amount of body fat of a person being weighed, comprising:
    (a) a buoyant member having sufficient buoyancy to support the apparatus and the weight of the person being weighed upon the surface of water and defining an opening therein;
    (b) a support member attached to said frame and extending across said opening;
    (c) a weighing platform suspended from said support member within said central opening; and
    (d) weighing means for measuring the weight of a person positioned upon said weighing platform.

5. An underwater weighing apparatus for measuring the relative amount of body fat of a person being weighed, comprising:
   (a) a buoyant frame having sufficient buoyancy to support the apparatus and the weight of the person being weighed upon the surface of water, said frame having a front portion; spaced side portions and a rear portion so as to define a central opening within said frame;
   (b) a support member having opposed, parallel end portions attached at their ends to one of side portions of said frame and extending upwardly therefrom, and a central portion extending between the upper ends of said end portions and extending across said central opening in said frame;
   (c) a weighing platform having a seat portion and brackets attached to opposite sides of said seat portion;
   (d) suspension means for suspending said weighing platform from said support member; and
   (e) weighing means for measuring the weight of a person positioned upon said weighing platform.

6. An underwater weighing apparatus according to claim 5, wherein said suspension means comprises one or more suspension attached at one end to said support member and at the other end to said weighing platform.

7. An underwater weighing apparatus according to claim 6, wherein said weighing means comprises a load cell attached to each of said cables.

8. An underwater weighing apparatus for measuring the relative amount of body fat of a person being weighed, comprising:
   (a) a buoyant frame having sufficient buoyancy to support the apparatus and the weight of the person being weighed upon the surface of water, said frame having a front portion, spaced side portions and a rear portion so as to define a central opening within said frame;
   (b) a support member having opposed, parallel end portions attached at their ends to one of side portions of said frame and extending upwardly therefrom, and a central portion extending between the upper ends of said end portions and extending across said central opening in said frame;
   (c) a weighing platform having a seat portion and brackets attached to opposite sides of said seat portion;
   (d) one or more suspension attached at one end to said support member and at the other end to said weighing platform; and
   (e) a load cell attached to each of said cables.

* * * * *